United States Patent
Keeton et al.

(10) Patent No.: US 6,878,373 B2
(45) Date of Patent: Apr. 12, 2005

(54) **PROBIOTIC COMPOSITION CONTAINING *BACILLUS CEREUS* RRRL B-30535**

(75) Inventors: Jimmie A. Keeton, Fort Collins, CO (US); Diane P. Williams, Hopkinton, MA (US)

(73) Assignee: MicroPure Technologies, Inc., Fort Collins, CO (US)

( * ) Notice: Subject to any disclaimer, the term of this patent is extended or adjusted under 35 U.S.C. 154(b) by 228 days.

(21) Appl. No.: 10/006,102

(22) Filed: Dec. 3, 2001

(65) Prior Publication Data

US 2003/0104091 A1 Jun. 5, 2003

(51) Int. Cl.$^7$ .............. B09B 3/00; C07G 17/00; C12N 1/00; C12N 1/20; D06M 16/00
(52) U.S. Cl. .............. 424/93.46; 435/252.5; 435/262.5; 435/264; 435/267; 435/834
(58) Field of Search .............. 424/93.46; 435/252.5, 435/262, 262.5, 264, 267, 834, 260, 282

(56) References Cited

U.S. PATENT DOCUMENTS

| | | | | |
|---|---|---|---|---|
| 4,999,193 A | | 3/1991 | Nguyen | 424/93 |
| 5,173,187 A | * | 12/1992 | Nader et al. | 210/614 |
| 5,627,275 A | * | 5/1997 | Roll | 536/23.7 |
| 5,698,246 A | * | 12/1997 | Villamar | 426/54 |
| 5,746,155 A | * | 5/1998 | Logan et al. | 119/230 |
| 6,025,152 A | * | 2/2000 | Hiatt | 435/42 |
| 6,034,124 A | | 3/2000 | Handelsman et al. | 514/488 |
| 2001/0033838 A1 | | 10/2001 | Farmer | |
| 2003/0003107 A1 | | 1/2003 | Farmer | |

OTHER PUBLICATIONS

"Interception and Inactivation of Phosphorus in Lakes and Ponds (Stopping the Problem at the Source)", by Chuck Zimney; Marine Biochemists—Illinois; http://www.marinebiochemists.com/phosarticle.html.
"LymnoZyme—How It Works*",http://www.lymnozyme.com/about.html.

KOI FAQ's http://www.lymnozyme.com/faq.html.

"*How the Family of Keeton Industries Microbia Aids Work and Helps the Aquatic KOI Pond System*"; http://www.lymnozyme.com/products.html.

Http://www.keetonaquatics.com/contactinfo.html.

* cited by examiner

*Primary Examiner*—David M. Naff
*Assistant Examiner*—Deborah K. Ware
(74) *Attorney, Agent, or Firm*—Dorsey & Whitney LLP

(57) ABSTRACT

A composition and method for reducing the levels of pathogenic bacteria in an aquatic environment. The composition includes isolated *Bacillus cereus* which are able to reduce a number of well known pathogenic bacterium from aquatic environments. The preferred *Bacillus cereus* is strain RRRL B-30535.

26 Claims, 7 Drawing Sheets

Figure 1. Probiotic composition reduces levels of pathogenic bacteria.

Figure 4. Probiotic composition reduces *Tilapia* fingerling mortality.

PROBIOTIC COMPOSITION CONTAINING *BACILLUS CEREUS* RRRL B-30535

FIELD OF THE INVENTION

The invention relates generally to a novel formulation for the control of pathogenic bacteria and more particularly to a probiotic formulation for the control of *Aeromonas, Pseudomonas, Vibrio, Streptococcus* and other pathogenic bacteria to fish, shellfish and other aquatic life. Furthermore, the invention relates to methods for controlling the levels of pathogenic bacteria, for promoting a healthy aquatic environment, and for promoting the health of aquatic organisms including particularly the reduction of fish morbidity and mortality. The compositions and methods are applicable in both freshwater and saltwater aquatic environments. The invention also has application for reducing pathogenic microbes in sewage or wastewater treatment facilities, specifically *Escherichia coli* or other pathogens not yet identified.

BACKGROUND OF THE INVENTION

Bacterial pathogens represent a substantial threat to aquatic environments, especially where the environment is heavily populated by fish, shellfish and other aquatic life. Aquatic environments having populations of pathogens are suboptimal for the health and development of various forms of aquatic life. Examples of such aquatic environments include a number of aquaculture type industries including, fish production facilities, where over 2.5 million pounds of fish are produced each year; freshwater and saltwater tropical fish aquariums, especially at the wholesale level where large populations of fish are combined for delivery and sale to potential customers; and koi and other outdoor ponds. Also included are intensive recirculating aquaculture systems, closed system aquaculture or other related intensive aquatic production systems containing aquatic life forms.

Prominent bacterial pathogens within the aquaculture industry include bacteria from the genus *Aeromonas, Vibrio, Pseudomonas, Streptococcus,* and *Columnaris*. These pathogens can lead to illness and death of the fish, shellfish or other aquatic life in the affected environment. The cost associated with these losses, and the potential health risk to those who consume the infected aquatic life is significant, and represents a major concern within these industries. Severe infections with pathogenic microbial species can result in mortalities approaching 80–90 percent.

Presently, bacterial pathogens are controlled by widespread use of substances such as chemicals and antimicrobial agents including antibiotics. However, widespread resistance to such treatments represents a major threat to the fish and shellfish populations as well as to those who consume or are associated with the resistant bacteria. Pathogenic bacterial resistance to chemicals and antimicrobials, as well as the lack of other effective treatments is of grave concern to the aquaculture industry. Against this backdrop the present invention has been developed.

SUMMARY OF THE INVENTION

In one aspect, compositions of the present invention include the isolation of an organism or organisms useful in the reduction of other bacteria, and preferably pathogenic bacteria, in an aquatic environment. One preferred isolate, strain EHC 100 is identified as belonging to the *Bacillus cereus* species of bacteria.

In another aspect, a method for reducing the levels of a bacteria, and preferably a pathogenic bacteria, in an aquatic environment includes providing the compositions of the present invention to the aquatic environment and monitoring the levels of pathogenic bacteria in the aquatic environment.

In another aspect, compositions of the present invention are used in the prevention of fish and shellfish mortality and in the treatment of fish and shell fish having a bacterially related disease.

These and various other features as well as advantages which characterize the present invention will be apparent from a reading of the following detailed description and a review of the associated figures.

DETAILED DESCRIPTION OF THE INVENTION

Probiotic Organism

As described more fully in the Examples below, a probiotic organism that reduces the levels of pathogenic bacteria in aquatic environments has been identified and characterized. The identified organism belongs to the *Bacillus* genus of bacteria, and in particular, belongs to the *Bacillus cereus* species of bacteria. According to the Biolog system of classification, the probiotic organism falls into Group 3 Gram-positive spore-forming rods. In precisely classifying the organism taxonomically, there may be instances of comparison where the identified organism appears similar to other organisms. For example, *Bacillus thuringiensis* (producer of insecticidal toxins) and *Bacillus anthracis* (etiological agent of anthrax) may be closely related to the identified organism. There is significant similarity among these organisms according to several aspects such as fatty acid analysis, and DNA sequence analysis including data regarding the intergenic space for ribosomal genes. The identified organism, however, is distinct in having the properties of significantly affecting the level of pathogenic bacteria in an aquatic environment and affecting fish health in aquaculture systems.

The probiotic organism of the present invention was identified using an activity assay, where a previously described waste and sludge reducer (K.I. Waste & Sludge Reducer, Keeton Industries, Fort Collins, Colo.) (hereinafter K.I. Reducer) was analyzed for its effects on *Aeromonas* and *Pseudomonas* levels in an aquatic environment. K.I. Reducer itself is used for control of accumulated organic waste and sludge in ponds, lakes, ornamental ponds, aquaria, and aquaculture facilities; also, it reduces nutrient levels through accelerated microbial decomposition of organic wastes on the pond bottom. In addition, K.I. Reducer also decreases the negative effects of eutrophication, the bio-oxygen-demand status, organic waste digestion and the rapid overgrowth of some bacteria and algae in aquatic environments.

From selected batches of the K.I. Reducer, smaller aliquots were prepared and tested for the ability to cause a decrease in pathogenic bacteria levels. Standard microbial isolation techniques and identifications using fatty acid analysis were performed on samples having the greatest effects on pathogenic bacteria reduction. Samples from a batch having the greatest activity were selected for further testing. Further testing showed that an isolated organism from K.I. Reducer showed significant activity in reducing pathogenic bacteria levels in aquatic environments. This isolate, designated strain EHC 100, was identified as a strain of the species *Bacillus cereus* by standard microbiological techniques and fatty acid analysis. This isolate has been deposited with the Agricultural Research Service Culture Collection (NRRL), 1815 North University Street, Peoria, Ill., having accession number B-30535. Note that as used herein, "isolated" refers to an organism of the present invention that has been separated from at least one contaminant found in the organisms natural environment or found in K.I. Reducer.

Formulations Of *Bacillus* EHC 100 strain were fermented and blended in solutions of 2 to 5% sodium. These blends were tested for the ability to reduce a level of pathogenic bacteria. Note that other like salts may be substituted for sodium.

The *Bacillus* EHC 100 strain compositions can be blended into other compositions that contain other species of beneficial microorgnisms. A blend can retain one or more than one property such as having the ability to reduce pathogenic bacteria in an aquatic environment and the ability to improve fish health.

Here, the terms "reduce" and "control" are used interchangeably and refer to a statistically significant difference in the level of a pathogenic bacteria in a target environment, or in the overall level of bacteria other than any composition used for treatment, when the difference relates to a level prior to treatment compared to a level following treatment.

Some conditions may affect the effectiveness of the compositions in an aquatic environment to reduce pathogenic bacteria or to improve fish health. In some cases, the effectiveness of any of the compositions can be dependent on the total alkalinity of the aquatic environment, or the temperature of the aquatic environment. For example, an aquatic environment having a temperature of about 50° F. to 62° F. may require an enhanced dose of the composition to produce the same effects as an aquatic environment at about 63° F. to 68° F. Therefore, there is likely a sliding scale of how much of the composition is required to produce the same effects on the aquatic environment dependent on the temperature of the aquatic environment. Other conditions that may affect effectiveness of compositions include whether a pond is heavily stocked or has poor filtering. Regardless, the dose of the composition may be varied to suit the conditions of the aquatic environment and produce the expected results.

Mechanisms of Action

The mechanisms of action are currently under investigation with regard to the ability of the compositions of the present invention to affect levels of pathogenic bacteria or to affect the health of aquatic organisms. All possible mechanisms of action for the present invention are not intended to limit the scope of the invention in any way and are all believed to be within the scope of the present invention.

One potential mechanism of action is for a composition of the present invention to directly compete with other bacteria, such as pathogenic species of bacteria for resources, such as nutrients in the aquatic environment. The compositions of the present invention may prevent other bacteria from maintaining or increasing their population levels. Such direct competition is effective in cases where the organisms, for example EHC100, in the composition are present initially with greater numbers, or in a case where an organism in 115 the composition grows at a greater rate than one or more other species of bacteria in the target aquatic environment.

A second potential mechanism involves indirect competition, where an organism in the composition fosters an environment that affects a third party organism in the aquatic environment. For example, the third party organism may then be in direct competition with the pathogenic species of bacteria in the aquatic environment.

A third potential mechanism involves the production of a molecule by an organism in the composition, for example EHC100, where the molecule acts either directly or indirectly upon a species of pathogenic bacteria in the aquatic environment. Such molecules could be peptides that function as toxins, or enzymes.

A fourth potential mechanism involves the production of a molecule by an organism in the composition, for example ECH100, that induces pathogen resistance in the aquatic organism population (similar to Systemic Acquired Resistance (SAR) in plants).

The possibility exists that some level of each mechanism is involved, independently or in combination, to give rise to the activities of the compositions described herein. It is also anticipated that an as of yet undiscovered mechanism of action may also be involved with the mechanisms of action of the present invention.

Culture Conditions

Initial compositions were isolated as pure cultures in standard media as known in the art such as nutrient agar or trypticase soy agar. Compositions that are embodiments of the present invention are grown in liquid broth cultures. The media can be a conventional media known in the art such as trypticase soy broth (TSB). Other enrichment media may also be used to grow compositions.

At the end of culturing, the density of the target organism is preferably between $4 \times 10^8$ and $6 \times 10^8$ cfu/mL, although greater or smaller concentrations may be attained and used according to the invention. In the cultures, about at least 80% of the colony forming units can be spores. In growing the cultures, a range of about 10° C. to 37° C. is used, preferably a range of 20° C. to 34° C. is used, and most preferably, a range of 28° C. to 30° C. is used. The cultures are incubated for about 12 to about 72 hours, and preferably for an amount of time required to reach the preferred cell density in a given culture medium.

A completed liquid culture can be stored at refrigeration temperatures or at room temperatures. Preferably, the cultures are stored at from about 3° C. to about 25° C. In another embodiment, the liquid culture may be dehydrated for storage and re-hydrated upon use. In yet another embodiment, the liquid culture may be lyophilized and 
stored. A culture may retain effectiveness for applications when stored for several months at room temperature and for over a year at refrigeration temperature.

Note that compositions may be used in aquatic applications in the presence of other products, for example, antibiotics which are well known in the art.

Applications

The organisms in compositions of embodiments of the invention are effective at reducing pathogenic bacteria levels in aquatic environments. In the methods of the invention, the pathogen-reducing effects of the present invention are achieved by treating an aquatic environment with one or more doses of a composition.

Dose sizes can range from about 20 mL to 60 mL of approximately $4\times10^8$ to approximately $6\times10^8$ organisms per 1,000 gallons of aquatic medium. Doses can be adjusted depending on a variety of factors including level of stocking, level of filtering, temperature, and alkalinity. Note that doses can be repeated as needed to achieve the desired result.

Other methods are envisioned to be within the scope of the present invention, including methods for treating a population of aquatic organisms such as fish or shellfish, methods for preventing bacterially transmitted disease in aquatic organisms, methods for improving an aquatic environment; methods for isolating an organism used to reduce pathogenic bacteria levels in an aquatic environment, where the desirable properties of the target organism are used to screen for the targeted organism; and the like. With respect to the present invention, "treatment" of fish or shellfish in an aquatic environment is meant to refer to any reduction in the percentage of fish or shellfish infected with a sufficient level of pathogenic bacterium that the fish or shellfish exhibit symptoms of the infection, for example, exhibit sores or blisters. A treatment, as such, is accomplished if a detectable number of fish or shellfish in the aquatic environment exhibit either fewer symptoms then before or have been alleviated of symptoms, by the compositions of the present invention being added to the environment.

Having generally described the invention, the same will be more readily understood by reference to the following examples, which are provided by way of illustration and are not intended as limiting.

EXAMPLE 1

Probiotic Solution Decreases Pathogenic Bacteria

Figure 1:
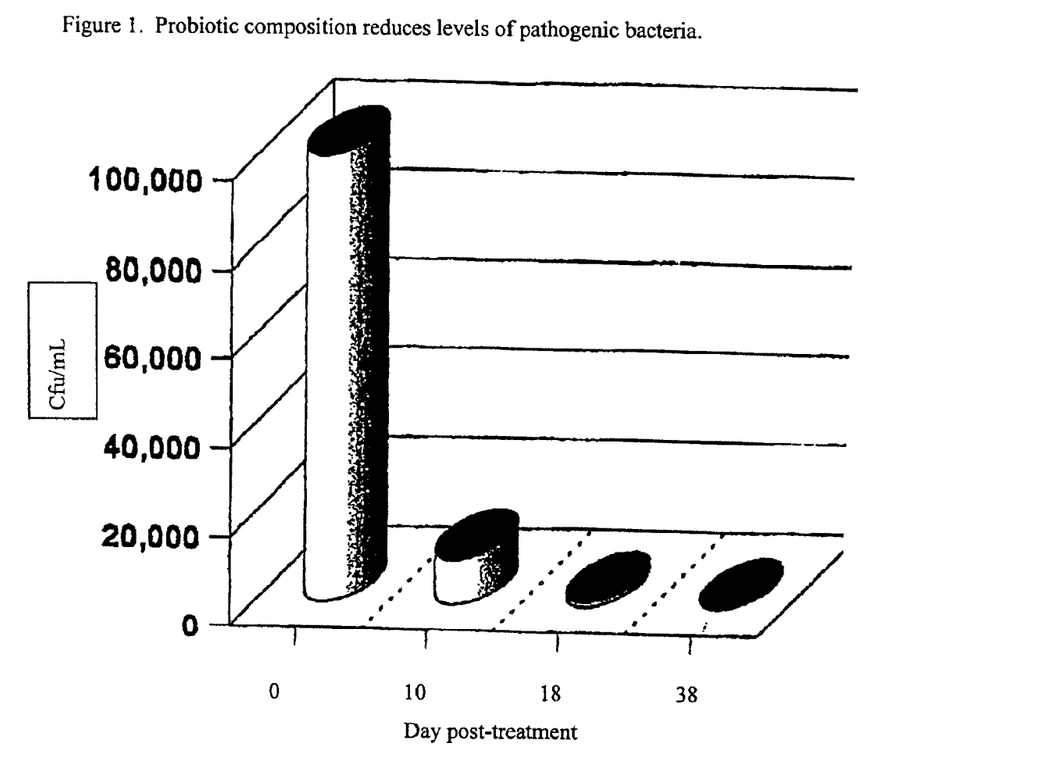
FIG. 1 illustrates a reduction in pathogenic bacteria levels in an aquatic environment treated with a composition in accordance with the present invention.

As shown in FIG. 1, addition of a volume of about 10–20 mL of product per 1,000 gallons system volume with a concentration of about $4\times10^8$ cfu/mL of *Bacillus* EHC 100 strain to an aquaculture system having up to approximately $10^5$ colonies per mL of *Streptococcus, Pseudomonas* and *Aeromonas* resulted in a dramatic decrease in the pathogens concentrations. Pathogens were substantially eliminated over the course of one month of treatment.

Similar results are shown in Table 1, where treatment of multiple strains of hemolytic streptococci with the probiotic composition reduced the level of hemolytic streptococci to undetectable levels as measured over a two-week period. Consistent results were observed a second experiment, also shown in Table 1. These experiments involved a commercial closed system Aquaculture Facility. A volume of about 10–20 mL of product per 1000 gallons system volume with a concentration of about $4\times10^8$ cfu/mL of the probiotic composition was used for an aquaculture environment having a volume capacity of about two million gallons. All analytical microbiological tests were performed by a certified laboratory using conventional methods as known in the art.

The data illustrates that the probiotic solutions of the invention are associated with a reduction in target pathogenic bacteria in an aquaculture environment.

Table 1 illustrates treatment with *Bacillus* EHC 100 strain in intensive aquaculture system. Beta hemolytic streptococcus was isolated in two production sytems at 2000 cfu/ml in system I and 1000 cfu/ml in system II, respectively. The systems were treated with three applications of strain EHC100 at the recommended dosage of 10–20 ml, *Bacillus* EHC 100 strain per 1000 gallons of system volume. Two weeks after the third application, no pathogenic beta hemolytic *Streptococcus* bacteria were found in the fish tank growout system.

The aquaculture tanks were screened for *Steptococcus* organisms only, as prior testing had confirmed that fish were infected with *Streptococcus.*

Figure 2:
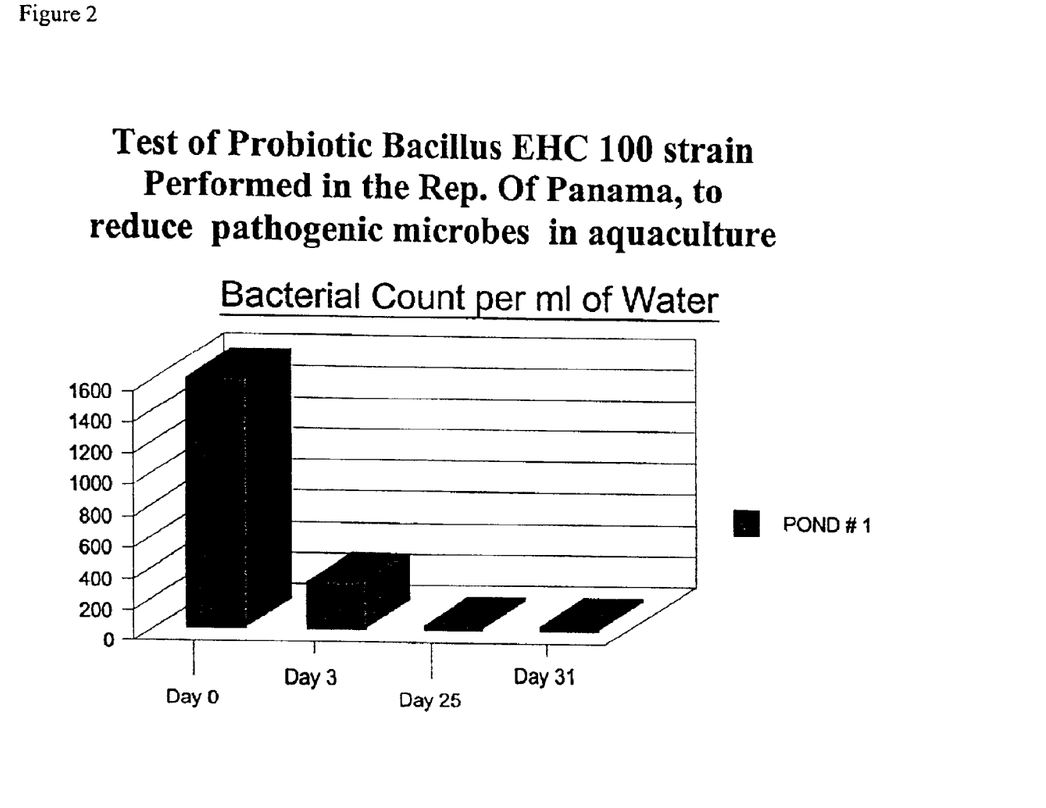
FIG. 2 illustrates a reduction in *Tilapia* fingerling mortality in an aquatic environment treated with a composition in accordance with the present invention.
Figure 3:
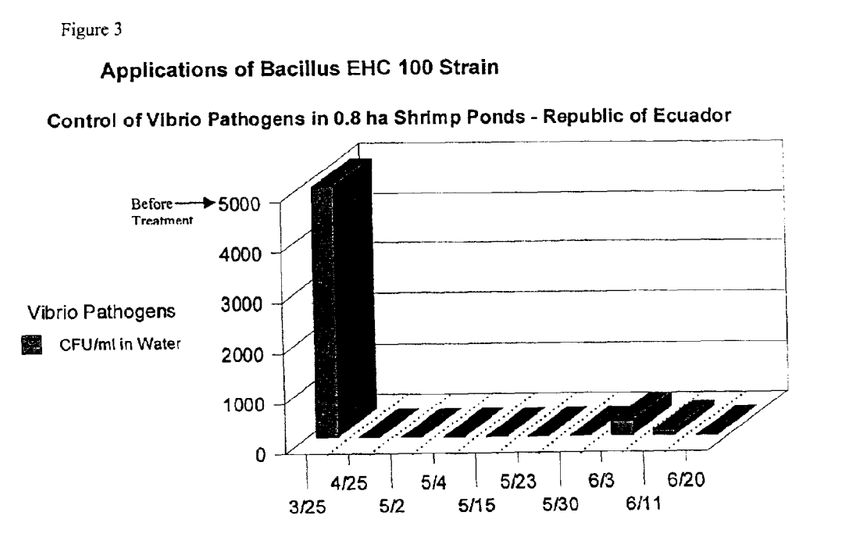
FIG. 3 illustrates a reduction in pathogenic bacteria levels in a koi pond treated with a composition in accordance with the present invention.
Figure 4:
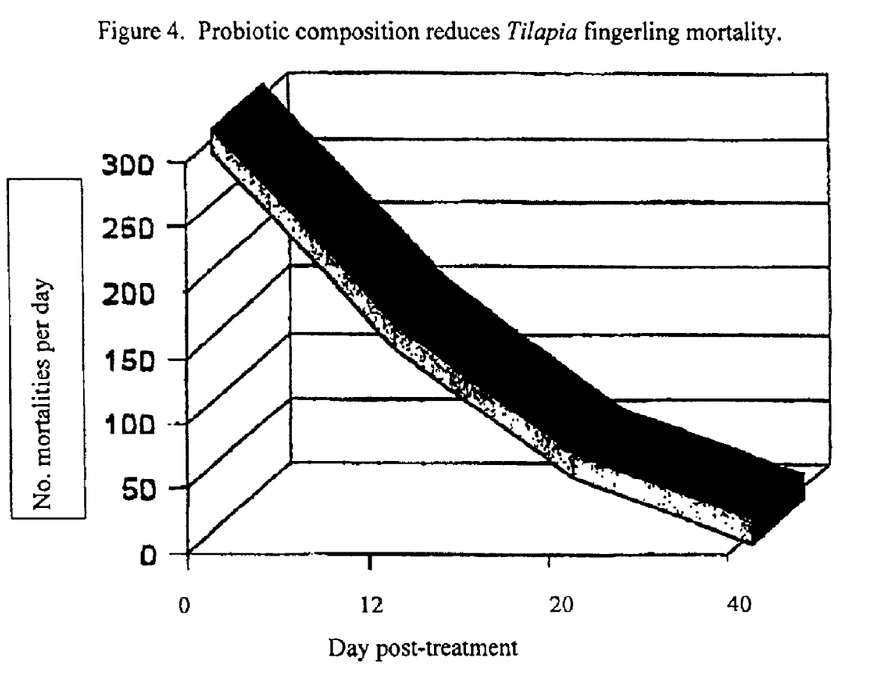
FIG. 4 illustrates a reduction in pathogenic bacteria levels in a koi pond treated with a composition in accordance with the present invention.

Further evidence that the probiotic strain EHC 100 causes a reduction in pathogenic organisms is provided in FIGS. 2 and 3. FIG. 2 illustrates a reduction of pathogenic organisms in outdoor shrimp ponds following treatments with *Bacillus* EHC 100 strain. Pathogenic organisms where isolated and identified as *Vibrio, Pseudomonas aeruginosa, Enterobacter* sp. And *Proteus* sp at the start of testing. Applications of *Bacillus* EHC 100 strain were added at a rate of 1 liter per 100,000 gallons of pond water, 1 treatment each 3 days for nine days followed by one weekly treatment for a 28 day period. Pathogenic organisms were decreased from 15,000 CFU/ml to 13 CFU/ml at the end of 28 day period. All tests were performed by qualified state pathologist at the Government Laboratory Of Diagnostic Veterinarial Science.

FIG. 3 provides a graph that depicts reduction of *Vibrio* bacterial pathogens in a 0.8 hectare intensive culture outdoor shrimp pond in the Republic of Ecuador. *Vibrio* was completely controlled by normal applications of *Bacillus cereus*, EHC 100 strain, during the entire 120 day growout cycle for shrimp *Paneaus vannemei* (White Shrimp)

TABLE 1

Effect of *B. cereus*, EHC 100 strain on control of pathogenic bacteria

| Site | Results: Control (cfu/mL) | Results: Treated (cfu/mL) |
|---|---|---|
| Experiment 1 | $2\times10^3$ 2000 hemolytic streptococci/ml before treatment | <No beta hemolytic strep detected two weeks after treatment. Detection limit of 1 CFU per mL of hemolytic streptococcus |
| Experiment 11 | $1\times10^4$ 1000 hemolytic streptococci/ml before treatment | <No beta hemolytic strep detected after two weeks after treatment detection limit of 1 CFU/ml streptococcus |

EXAMPLE 2

Probiotic Solution Decreases Tilapia Mortality

As shown in FIG. 4, probiotic solution treatment of *Tilapia* fingerlings resulted in a significant decrease in mortality. Approximately one liter of probiotic solution having a concentration of $4\times10^8$ bacillus of the invention was added per 100,000 gallons of system volume three times in 9 days followed by weekly treatments over a four week period. Fingerling mortality was monitored over a four week period.

The data illustrates that the probiotic solutions of the invention have a positive effect in reducing the mortality of treated aquatic populations. 
EXAMPLE 3

Probiotic Solution Decreases Pathogenic Bacteria

Figure 5:
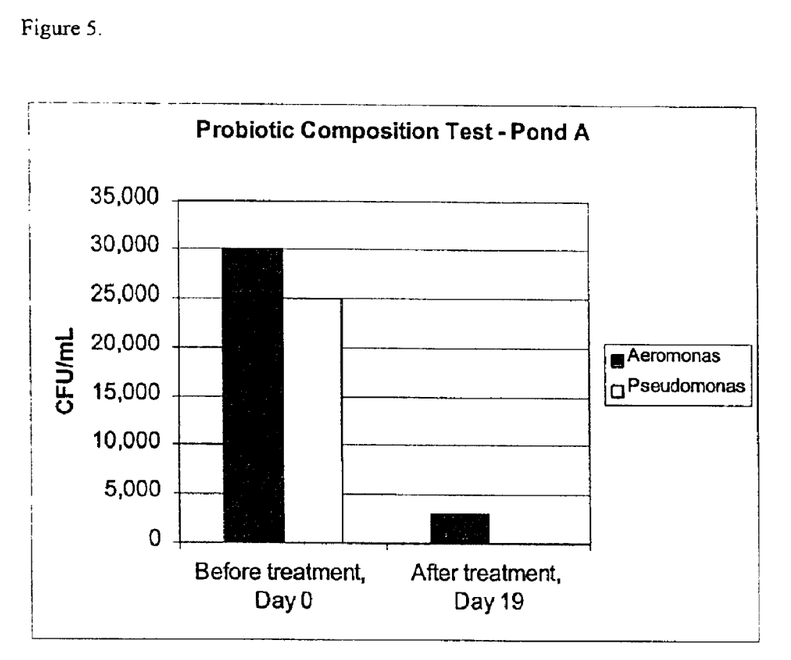
FIG. 5 illustrates a reduction in pathogenic bacteria levels in a koi pond treated with a composition in accordance with the present invention.
Figure 6:
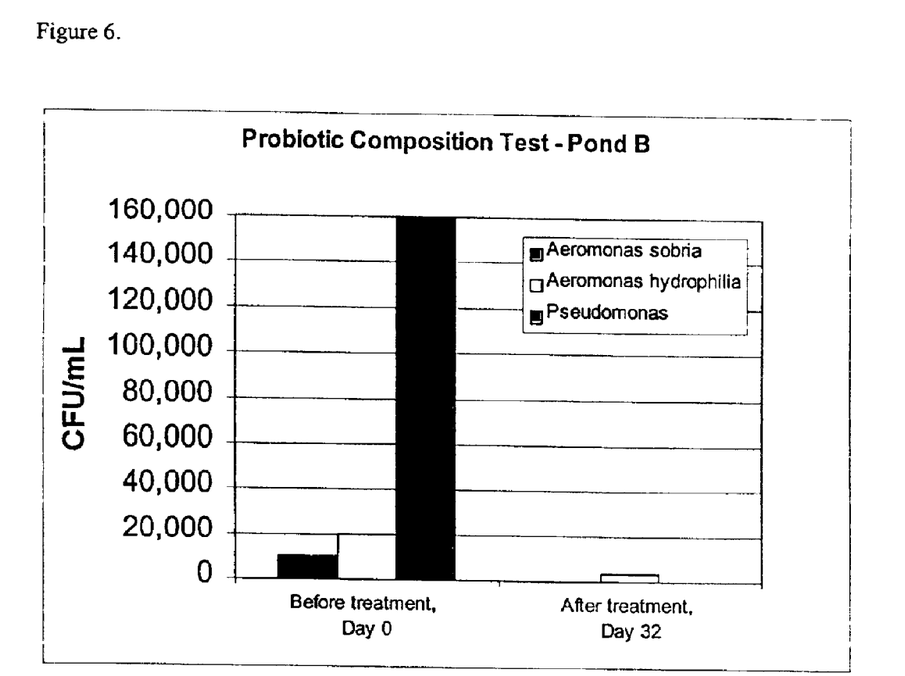
FIG. 6 illustrates a reduction in pathogenic bacteria levels in an aquaculture with a *Bacillus* EHC 100 strain of the present invention.
Figure 7:
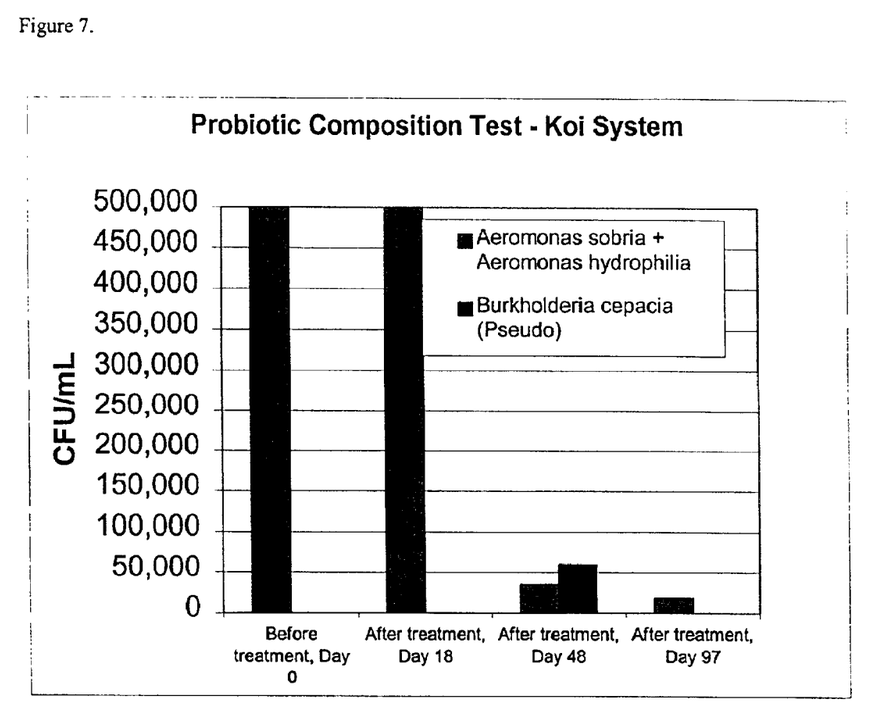
FIG. 7 illustrates a reduction in vibrio pathogens in 0.8 ha shrimp ponds using the *Bacillus* EHC 100 strain of the present invention.

As shown in FIGS. 5, 6, and 7, and Table 2, addition of a probiotic solution of the present invention to various aquatic systems including ponds resulted in a significant decrease in the pond water levels of certain target pathogenic bacteria.

In these examples, the concentration of bacteria of the composition in the initial 20 ml dose was about $4 \times 10^8$ CFU/mL to $6 \times 10^8$ CFU/mL.

FIG. 5 shows the results of treating Pond A with a composition at a dose rate of 20 mL per 1,000 gallons of aquatic medium. Pond A water initially having approximately 25,000 to 30,000 *Aeromonas* and *Pseudomonas* cfu/mL was treated with a probiotic solution of the invention. A period of treatment lasting about 19 days resulted in a significant decrease in the pathogens levels: below 3,000 cfu/mL for *Aeromonas* and undetectable levels for *Pseudomonas*.

FIG. 6 shows the results of treating Pond B water with a composition at a dose rate of 20 mL per 1,000 gallons of aquatic medium. Pond B water initially had levels of bacteria as follows: *Aeromonas sobria* at 10,000 cfu/mL, *Aeromonas hydrophilia* at 20,000 cfu/mL, and *Pseudomonas* at 160,000 cfu/mL. A period of treatment lasting about 32 days resulted in a significant decrease in the pathogens levels. At the end of the treatment period, the following levels were observed: *Aeromonas sobria* was undetectable, *Aeromonas hydrophilia* at 3,000 cfu/mL, and *Pseudomonas* was undetectable.

FIG. 7 shows the results of treating a koi system with a composition at a dose rate of 20 mL per 1,000 gallons of aquatic medium and at a dose rate of 60 mL per 1,000 gallons. The koi system water initially had levels of bacteria as follows: *Aeromonas sobria/hydrophilia* at 500,000 cfu/mL, and *Burkholderia cepacia* (Pseudo) at an undetectable level. Several treatment periods were examined, including periods of 18, 48, and 97 days. After the initial treatment at a dose rate of 20 mL per 1,000 gallons, an assessment was made at 18 days. At 18 days, the following levels were observed: *Aeromonas sobria/hydrophilia* at 500,000 cfu/mL, and *Burkholderia cepacia* (Pseudo) at an undetectable level.

After the 18 day period, the dose rate was increased to 60 ml per 1,000 gallons. After 48 days, a significant change was noted in at least one population of bacteria. At 48 days, the following levels were observed: *Aeromonas sobria/hydrophilia* at 35,000 cfu/mL, and *Burkholderia cepacia* (Pseudo) at level of 60,000 cfu/mL. After 97 days, the following levels were observed: *Aeromonas sobria/hydrophilia* at 16,000 cfu/mL, and *Burkholderia cepacia* (Pseudo) at an undetectable level. Thus the treatment ultimately resulted in a reduction of more than 10-fold for *Aeromonas* species after 48 days, with a reduction of more than 25-fold after 97 days.

Treatments during the first 18 days were standard dosing of 20 ml/1000 gallon system water, one treatment every 3 days for 9 days, followed by once per week.

Some of these experiments involved an outdoor pond. All analytical microbiological tests were performed by a certified laboratory using conventional methods as known in the art.

TABLE 2

Data supporting FIGS. 5, 6, and 7.

| FIG. 5 | Organism | Before treatment, Day 0 | After treatment, Day 19 | | |
|---|---|---|---|---|---|
| | Aeromonas | 30,000 | 3,000 | | |
| | Pseudomonas | 25,000 | none detected | | |

| FIG. 6 | Organism | Before treatment, Day 0 | After treatment, Day 32 | | |
|---|---|---|---|---|---|
| | Aeromonas sobria | 10,000 | none detected | | |
| | Aeromonas hydrophilia | 20,000 | 3,000 | | |
| | Pseudomonas | 160,000 | none detected | | |

| FIG. 7 | Organism | Before treatment, Day 0 | After treatment, Day 18 | After treatment, Day 48 | After treatment, Day 97 |
|---|---|---|---|---|---|
| | Aeromonas sobria + Aeromonas hydrophilia | 500,000 | 500,000 | 35,000 | 18,000 |
| | Burkholderia cepacia (Pseudo) | none detected | none detected | 60,000 | none detected |

EXAMPLE 4

EHC100 has a Fatty Acid Composition Consistent with that of *Bacillus cereus*

The fatty acid composition of an individual species of bacteria can serve as a reliable identifying characteristic. In general, a sample of unknown bacteria is cultured and its fatty acids extracted for separation by gas chromatography. A computer generated profile of the separated fatty acids (having from 9 to 20 carbons in length) is compared to profiles for over 2600 species in a Microbial Identification System (Sherlock Libraries). Matches are determined through statistical probability software.

Fatty acid analysis on a target sample can be performed by a commercial laboratory, for example, Acculab, 223 Lake Drive, Pancader Corporate Center, Newark, Del. Briefly, Acculab receives a target culture, grows and harvests the bacteria, and places the bacteria in an extraction tube. One ml of a saponification solution (90 g sodium hydroxide mixed with 300 ml methanol and 300 ml $dH_2O$) is added to the sample and the sample is heated in a boiling water bath for 5 minutes. Samples are removed from the water bath and vortexed for about 5 seconds. The samples are returned to the water bath for an additional 25 minutes at which time it is removed and cooled in tap water. Two mls of methylation solution (405 mls of 6 N hydrochloric acid added to 345 ml of methyl alcohol) is added to the sample and the sample is heated for about 9 to 11 minutes at 79 to 81° C. The sample is removed and cooled in tap water. Approximately 1.5 mls of extraction solution (400 ml of hexane mixed with 400 ml of methyl tert-butyl ether) is then added to the sample and the sample is gently tumbled for about 10 minutes. The aqueous lower phase is discarded and 3 mls of base wash (9 g sodium hydroxide dissolved in 750 ml $dH_2O$) is added for an additional 5 minute incubation. Approximately ⅔ of the organic phase is removed and analyzed by gas chromatography (MIDI BIO-GC, Hewlett-Packard) using a fused silica capillary column (coated with 5% phenyl methyl silicone). GC generated data is analyzed using MIDI BIO-GC software.

Results are computed to provide a numeric value which expresses how closely the fatty acid composition of the unknown sample compares with the mean fatty acid compositions of the strains used to create the Sherlock Library. A value with a similarity above 0.5 or higher and more than 0.1 separation between the first and second entry is considered a good library comparison.

As shown in Table 3, EHC100 has a fatty acid composition that likely corresponds to the fatty acid composition of *Bacillus cereus*. A sample of EHC100 was isolated using methods in accordance with the present invention and supplied to Acculab. The EHC100 sample showed a 0.752 value, which was over 0.1 greater than the next entry –0.619 (*Bacillus canadensis*), indicating that there is a good likelihood that EKC100 is a *Bacillus cereus*.

What is claimed is:

1. A probiotic composition for reduction of a pathogenic in an aquatic environment consisting of:
    a biologically pure bacterium of the genus *Bacillus cereus* strain RRRL B-30535.

2. The composition of claim 1 wherein the bacterium being reduced is a pathogenic bacterium selected from the group consisting of *Streptococcus, Pseudomonas* and *Aeromonas*.

3. The composition of claim 1 further comprising from 2 to 5% sodium.

4. The composition of claim 1 wherein the biologically pure bacterium has a density of from $4 \times 10^8$ to $6 \times 10^8$ colony forming units per milliliter.

5. The composition of claim 4 wherein the colony forming units of the *Bacillus cereus* are less than 99% spores.

6. The composition of claim 4 wherein the colony forming units of the *Bacillus cereus* are less than 80% spores.

7. The composition of claim 1 wherein the aquatic environment is a Koi pond.

TABLE 3

Acculab Generated Profile and Similarity Index for EHC100

| RT | Area | Ar/Ht | Respon | ECL | Name | % | Comment 1 | Comment 2 |
|---|---|---|---|---|---|---|---|---|
| 1.597 | 447011437 | 0.028 | | 7.014 | SOLVENT PEAK | | <min rt | |
| 1.698 | 17350 | 0.016 | | 7.222 | | | <min rt | |
| 1.781 | 7784 | 0.133 | | 7.394 | | | <min rt | |
| 4.247 | 493 | 0.028 | 1.060 | 11.608 | 12:0 ISO | 0.36 | ECL deviates –0.001 | Reference 0.006 |
| 5.279 | 10541 | 0.032 | 1.014 | 12.614 | 13:0 ISO | 7.39 | ECL deviates –0.000 | Reference 0.006 |
| 5.378 | 1491 | 0.034 | 1.011 | 12.703 | 13:0 ANTEISO | 1.04 | ECL deviates –0.001 | Reference 0.008 |
| 6.535 | 6617 | 0.035 | 0.981 | 13.619 | 14:0 ISO | 4.49 | ECL deviates –0.000 | Reference 0.006 |
| 7.044 | 3013 | 0.038 | 0.972 | 14.000 | 14:0 | 2.03 | ECL deviates –0.000 | Reference 0.006 |
| 7.983 | 46631 | 0.039 | 0.960 | 14.623 | 15:0 ISO | 30.96 | ECL deviates –0.000 | Reference 0.005 |
| 8.119 | 8302 | 0.039 | 0.958 | 14.713 | 15:0 ANTEISO | 5.50 | ECL devialea –0.000 | Reference 0.005 |
| 8.553 | 387 | 0.035 | 0.954 | 15.000 | 15:0 | 0.26 | ECL deviates –0.000 | Reference 0.005 |
| 9.188 | 1951 | 0.040 | 0.949 | 15.389 | 16:1 w7c alcohol | 1.28 | ECL deviates –0.002 | |
| 9.344 | 4971 | 0.041 | 0.948 | 15.484 | Sum In Feature 2 | 3.26 | ECL deviates –0.004 | 16:1 ISO I/14:0 3OH |
| 9.577 | 11222 | 0.046 | 0.946 | 15.626 | 16:0 ISO | 7.35 | ECL deviates –0.001 | Reference 0.003 |
| 9.793 | 685 | 0.042 | 0.945 | 15.758 | 16:1 w11c | 0.45 | ECL deviates –0.001 | |
| 9.956 | 15800 | 0.044 | 0.944 | 15.858 | Sum In Feature 3 | 10.32 | ECL deviates –0.006 | 15:0 ISO 2OH/16:1w7c |
| 10.190 | 6079 | 0.044 | 0.943 | 16.000 | 16:0 | 3.97 | ECL deviates –0.000 | Reference 0.004 |
| 10.562 | 1606 | 0.045 | 0.942 | 16.218 | 15:0 2OH | 1.05 | ECL deviates –0.001 | |
| 10.855 | 6613 | 0.045 | 0.940 | 16.390 | ISO 17:1 w10c | 4.30 | ECL deviates –0.002 | |
| 10.979 | 7824 | 0.047 | 0.940 | 16.462 | ISO 17:1 w5c | 5.09 | ECL deviates –0.001 | |
| 11.118 | 2078 | 0.044 | 0.940 | 16.543 | 17:1 ANTEISO A | 1.35 | ECL deviates –0.003 | |
| 11.267 | 12573 | 0.043 | 0.939 | 16.631 | 17:0 SIO | 8.17 | ECL deviates –0.001 | Reference 0.005 |
| 11.424 | 2141 | 0.044 | 0.939 | 16.723 | 17:0 ANTEISO | 1.39 | ECL deviates –0.000 | Reference 0.004 |
| | 4971 | | | | SUMMED FEATURE 2 | 3.26 | 12:0 ALDE? | unknown 10.928 |
| | | | | | | | 16:1 ISO I/14:0 3OH | 14:0 3OH/16:1 ISO I |
| | 15800 | | | | SUMMED FEATURE 3 | 10.32 | 16:1 w7c/15 iso 2OH | 15:0 ISO 2OH/16:w7c |

| Solvent AR | Total Area | Named Area | % Named | Total Amnt | Nbr Ref | ECL Deviation | Ref ECL Shift |
|---|---|---|---|---|---|---|---|
| 447011437 | 151017 | 151017 | 100.00 | 144550 | 12 | 0.002 | 0.005 |

| | Similarity Index |
|---|---|
| TSBA40 (Rev 4.10) Bacillus | 0.752 |
| B. cereus | 0.752 |
| B.c.GC subgroup A* | 0.752 |
| B. thuringiensis canadensis sv.** | 0.619 |
| B. thuringiensis kurstakii** | 0.523 |

It is understood for purposes of this disclosure, that various changes and modifications may be made to the invention that are well within the scope of the invention. Numerous other changes may be made which will readily suggest themselves to those skilled in the art and which are encompassed in the spirit of the invention disclosed herein.

The specification contains citations to references such as patents, patent applications, and publications. Each is hereby incorporated by reference for all purposes.

8. The composition of claim 1 wherein the aquatic environment is saltwater.

9. The composition of claim 1 wherein the aquatic environment is a shrimp pond.

10. The composition of claim 1 wherein the aquatic environment is freshwater.

11. A method for treating fish infected with pathogenic bacteria in an aquatic environment comprising:

adding a sufficient amount of the composition of claim 1 to the aquatic environment to cause a reduction in a percentage of fish infected with the pathogenic bacteria.

12. A method for treating shellfish infected with pathogenic bacteria in an aquatic environment comprising:

adding a sufficient amount of the composition of claim 1 to the aquatic environment to cause a reduction in a percentage of shellfish infected with the pathogenic bacteria.

13. A method for reducing levels of pathogenic bacteria in an aquatic environment comprising:

adding a sufficient amount of the composition of claim 1 to the aquatic environment to cause a reduction in the pathogenic bacteria.

14. The method of claim 13 further comprising:

determining a level of pathogenic bacteria in the aquatic environment before and after addition of the composition; and adding a second dose of the composition to the aquatic environment to cause a further reduction in the pathogenic bacteria.

15. The method of claim 13 wherein 20 to 60 milliliters of the composition having from $4 \times 10^8$ to $6 \times 10^8$ of the *Bacillus cereus* is added per 1,000 gallons of aquatic environment.

16. The method of claim 13 wherein the aquatic environment is a Koi pond.

17. The method of claim 13 wherein the aquatic environment is saltwater.

18. The method of claim 13 wherein the aquatic environment is freshwater.

19. A method for reducing the levels of fish morbidity in an aquatic environment comprising:

adding a sufficient amount of the composition of claim 1 to the aquatic environment to cause a reduction in a pathogenic bacteria in the aquatic environment.

20. The method of claim 19 further comprising:

determining a level of pathogenic bacteria in the aquatic environment before and after addition of the composition;

determining an approximate number of fish in the aquatic environment before and after the addition of the composition to the aquatic environment; and adding a second dose of the composition to the aquatic environment to cause a further reduction in the pathogenic bacteria.

21. The method of claim 19 wherein the fish is *Tilapia*.

22. The method of claim 19 wherein 20 to 60 milliliters of the composition having from $4 \times 10^8$ to $6 \times 10^8$ of the *Bacillus cereus* is added per 1,000 gallons of aquatic environment.

23. The method of claim 19 wherein the aquatic environment is a Koi pond.

24. The method of claim 19 wherein the aquatic environment is a shrimp pond.

25. The method of claim 19 wherein the aquatic environment is saltwater.

26. The method of claim 19 wherein the aquatic environment is freshwater.

* * * * *

UNITED STATES PATENT AND TRADEMARK OFFICE
CERTIFICATE OF CORRECTION

PATENT NO. : 6,878,373 B2  
DATED : April 12, 2005  
INVENTOR(S) : Jimmie A. Keeton and Diane P. Williams It is certified that error appears in the above-identified patent and that said Letters Patent is hereby corrected as shown below:

<u>Column 10,</u>
Line 2, delete "bacterium" and insert -- bacterium --.
Line 4, insert -- pathogenic -- before "bacterium".

Signed and Sealed this

Seventh Day of June, 2005

JON W. DUDAS
*Director of the United States Patent and Trademark Office*

UNITED STATES PATENT AND TRADEMARK OFFICE
CERTIFICATE OF CORRECTION

PATENT NO. : 6,878,373 B2
DATED : April 12, 2005
INVENTOR(S) : Jimmie A. Keeton and Diane P. Williams It is certified that error appears in the above-identified patent and that said Letters Patent is hereby corrected as shown below:

<u>Column 10,</u>
Line 2, delete "a pathogenic" and insert -- bacterium --.
Line 4, insert -- pathogenic -- before "bacterium".

This certificate supersedes Certificate of Correction issued June 7, 2005.

Signed and Sealed this

Twenty-third Day of August, 2005

JON W. DUDAS
*Director of the United States Patent and Trademark Office*